United States Patent [19]

Brandley et al.

[11] Patent Number: 5,035,786

[45] Date of Patent: * Jul. 30, 1991

[54] FLUORESCENT TAG FOR SUGAR ELECTROPHORESIS

[75] Inventors: Brian K. Brandley, Alameda; Michael Tiemeyer, Oakland, both of Calif.

[73] Assignee: Glycomed, Incorporated, Alameda, Calif.

[*] Notice: The portion of the term of this patent subsequent to Dec. 4, 2007 has been disclaimed.

[21] Appl. No.: 483,043

[22] Filed: Feb. 16, 1990

[51] Int. Cl.$^5$ ................... C07H 1/06; C07H 3/00; C25B 7/00

[52] U.S. Cl. ................... 204/182.1; 204/182.8; 204/299 R; 204/180.1; 536/127

[58] Field of Search ............... 204/180.1, 182.1, 182.8, 204/299 R; 536/127

[56] References Cited

U.S. PATENT DOCUMENTS

| | | | |
|---|---|---|---|
| 4,109,075 | 8/1978 | Deaton | 536/127 |
| 4,305,799 | 12/1981 | Schwarz et al. | 204/182.1 |
| 4,666,581 | 5/1987 | Itoh et al. | 204/182.1 |

FOREIGN PATENT DOCUMENTS

88/10422  12/1988  PCT Int'l Appl.

OTHER PUBLICATIONS

Takara Shuzo Company, Ltd.; Central Research Labs, Kyoto, Japan, Carbohydrate Analysis System Catalog—13 pgs.

*Primary Examiner*—John F. Niebling
*Assistant Examiner*—David G. Ryser
*Attorney, Agent, or Firm*—Irell and Manella

[57] ABSTRACT

A method of separating mixtures of saccharides into distinct detectable groups is disclosed. The method comprises modifying 1-amino-4-naphthalene sulfonic acid (ANSA) with a light-sensitive azido-group and binding the modified ANSA to saccharides to form ANSA/saccharide conjugates. The conjugates are subjected to electrophorectic separation to obtain separate groups of conjugates in the gel. The groups of conjugates are transferred from the gel to the surface of a membrane which is exposed to light for a sufficient time and light frequency to activate the azido-group. The light-activated azido-groups attached to the surface of the membrane. The ANSA/saccharides conjugates can then be contacted with labeled probes such as radiolabeled proteins to determine the affinity of the probes to particular saccharides.

22 Claims, No Drawings

FLUORESCENT TAG FOR SUGAR ELECTROPHORESIS

CROSS-REFERENCE

This application is related in part to two other co-pending U.S. applications filed concurrently with the present application on Feb. 16, 1990. One related application is application Ser. No. 07/481,361, which application is entitled "Two-Dimensional Electrophoretic Separation of Carbohydrates" invented by Brian K. Brandley, a co-inventor of the present invention; the other application is application Ser. No. 07/481,367, which application is entitled "Electro-Blotting of Electrophoretically Resolved Fluorescent-Labeled Saccharides and Detection of Active Structures With Protein Probes" invented by Brian K. Brandley, Paul G. James and Michael Tiemeyer, who are co-inventors working in the same research organization as the present inventors with an obligation to assign the invention to the same entity. The above-referenced applications are each incorporated herein by reference in their entireties.

FIELD OF THE INVENTION

This inventions relates generally to the field of electrophoretic separation and electro-blotting techniques. More specifically, the invention relates to separating mixtures of saccharides with electrophoresis and electro-blotting the separated saccharides while using a fluorescent tag which binds to and charges the saccharides and a light-activatable azido-group.

BACKGROUND OF THE INVENTION

Electrophoresis is a well known technique for the separation of a charged species by utilizing their differences in rate of migration under the influence of an electrical field. The procedure has proved invaluable for the resolution and isolation of complex biological substances such as enzymes, serums, carbohydrates, proteins, DNA and RNA. Most analytical electrophoresis methods are based on zone-electrophoresis in which a thin zone of a sample material is applied to the electrophoretic medium. The electrophoretic migration of the sample components results in the formation of fractional zones. These zones can be examined and studied by applications of standard electrophoretic practice such as fixing, staining and washing to remove buffers. Desirably, the electrophoretic media is a thin gel film coated on a suitable support, commonly glass or plastic. Such an arrangement permits the electrophoretic separation to be achieved in a minimum of time with a maximum degree of resolution.

Various hydrophilic colloids, for example, starch, agarose and cellulose derivatives have been used in forming electrophoretic gel films, but polyacrylamide is preferred. One reason for preferring polyacrylamide is that gels can be prepared from it having a wide range of pore size. This is accomplished primarily by varying the ratio of acrylamide polymer to the N, N', methylenebisacrylamide cross-linking reagent.

The resulting polyacrylamide gels provide high resolution electrophoretic separation of important biopolymers, for example, proteins and nucleic acids. In addition, the absence of ionized groups in polyacrylamide gels render such gels suitable as an anticonvection medium for isoelectric focusing.

Once the electrophoretic techniques have been applied in order to separate the materials in the gel, it is necessary to transfer the separated materials from the gel to a support where they can be tested. A number of procedures are available for transferring the electrophoretically resolved materials from the gel. One such procedure involves electro-blotting. This type of transfer procedure involves transferring the resolved bands within the gel to a support matrix such as a nitrocellulose sheet. The transfer is carried out by the application of an electric field and therefore is distinguishable from a more conventional alternative which involves the capillary transfer of such materials usually used in techniques such as southern and northern blotting.

SUMMARY OF THE INVENTION

The present invention provides a method for separating mixtures of saccharides into distinct detectable groups. The method is carried out by reacting a mixture of saccharides with a modified form of 1-amino-4-naphthalene sulfonic acid (hereinafter ANSA) in order to form saccharide/ANSA conjugates. An important aspect of the invention involves the modification of the ANSA molecules by the addition of a light-sensitive azido-group. After the conjugates are formed, they are subjected to gel electrophoresis for a sufficient period of time to form separate groups of conjugates in bands in the electrophoresis gel. The bands of conjugates are transferred from the gel to the surface of a membrane by electro-blotting procedures. Thereafter, the conjugates on the surface of the substrate are subjected to light for a sufficient period of time and a sufficient frequency in order to activate the light-sensitive azido-group which when activated substantially increases the affinity of the group to the membrane surface. The securely bound conjugates can be visually detected because the ANSA will fluoresce when exposed to U.v. light. The fluorescent conjugates can then be contacted with labeled probes, such as labeled protein probes, in order to determine the affinity of the protein to particular groups of saccharides.

A primary object of the invention is to provide a method of separating mixtures of saccharides into distinct detectable groups which can then be readily assayed for their affinity to particular molecules, such as proteins attached to detectable probes.

An advantage of the present invention is that the separation procedure provides visually detectable distinct groups of saccharides on a substrate surface.

A feature of the present invention is that the separated groups of saccharides provided on a substrate surface by electro-blotting are caused to have greater affinity for the substrate surface by a light activatable azido-group attached to the ANSA.

These and other objects, advantages and features of the present invention will become apparent to those persons skilled in the art upon reading the details of the structure, synthesis and usage as more fully set forth below, reference being made to the accompanying general structural formula forming a part hereof.

DETAILED DESCRIPTION OF PREFERRED EMBODIMENTS

Before the present invention for separating, labeling and testing oligosaccharides is described, it is to be understood that this invention is not limited to the particular oligosaccharides, labels, proteins or process steps described as such compounds and steps may, of course, vary. It is also to be understood that the terminology used herein is for purposes of describing particular embodiments only and is not intended to be limiting since the scope of the present invention will be limited only by the appended claims.

It must be noted that as used in the specification and the appended claims, the singular forms "a", "an" and "the" include plural referents unless the context clearly dictates otherwise. Thus, for example, reference to "a saccharide" includes mixtures of saccharides, reference to "an azido-group" includes reference to mixtures of such groups, and reference to "the electrophoretic processing step" includes a variety of similar steps of type described herein.

In order to carry out the present invention, a modified form of a 1-amino-4-naphthalene sulfonic acid (ANSA) must be prepared. The modified ANSA is prepared by reacting the ANSA with a light-sensitive azido-group. The azido-group is of course kept out of contact with the light (capable of activating the group) prior to and during the reaction.

The 1-amino-4-naphthalene sulfonic acid (ANSA) used in connection with the present invention has the following structure:

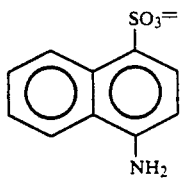

The $-NH_2$ amino group is indicated as being at the "1" position and the $-SO_3=$ group is at the "4" position. The shared double bonds in each ring structures provides the fluorescent character to the ANSA when the ANSA is exposed to U.V. light.

The ANSA molecule is modified by the attachment of an azido-group which can be attached at any one of the positions either not already occupied by either the $-SO_3=$ or the $-NH_2$ groups. The azido-group is the $-N_3$ group which may be connected directly to the ring structure or connected via a linking group. The azido-group will connect at the 5, 6, 7 or 8 position of the ANSA.

After the azido-group modified light-sensitive ANSA compound is prepared, it is reacted with a mixture of saccharide compounds to be tested. The ANSA is bound to the saccharides in the mixture by connecting the saccharide to the ring structure of the ANSA at a position not previously occupied, thus forming saccharide/ANSA conjugates. These conjugates are formed in order to provide the saccharide molecules with: (1) a charge (obtained from the $-SO_3=$ of the ANSA) which is necessary in order to carry out electrophoretic separation of the saccharide compounds; and (2) a U.V. light fluorescent ability (obtained from the shared double bonds of ring structures of the ANSA).

The saccharide/ANSA conjugates are then subjected to gel electrophoresis for a sufficient period of time to form separate groups of conjugates in the gel electrophoresis. The groups are generally present in the gel in specific bands which related in large part to the size, but also relate to the specific structure of the saccharides.

The separation techniques utilized in connection with the present invention have been found to work particularly well in connection with smaller saccharides. More specifically, the gel electrophoresis has been found to be particularly useful in separating mixtures of monosaccharides, disaccharides, and trisaccharides. Conventional procedures are generally not capable of providing sufficient resolution to separate away smaller saccharides into distinct bands. The addition of the ANSA group provides a sufficient amount of charge to allow for the separation of the smaller saccharides into distinct groups but does not apply too much charge so that the charge quality overwhelms any other quality of the saccharides and thus does not provide for resolution among different types of closely related saccharides. Further, the shared double bonds within the ring structures of the ANSA provide for the fluorescent capability of the conjugates formed. Accordingly, when different bands of saccharides are separated away from each other, it is possible to visually view these bands simply by the application of ultraviolet light.

The use of such a fluorescent tag provides a number of advantages over and above the use of other types of tags. For example, a fluorescent tag is substantially safer and less expensive than the use of a radiolabel. Further, the use of a fluorescent tag is substantially less cumbersome and more efficient than the use of antibody-linked enzyme tags. These advantages are obtained concurrently with the overall advantage of providing a tag which allows for greatly improved resolution especially as used in connection with smaller saccharide compounds.

The separated bands of conjugates within the gel are then transferred to the surface of a membrane. A number of different types of membrane surfaces can be utilized in connection with the invention. However, nylon is preferable. The transfer of the saccharide/ANSA conjugates from the gel to the surface of the substrate is carried out by utilizing electro-blotting techniques. The electro-blotting is carried out for a sufficient period of time to allow substantial amounts of the conjugates within the gel to transfer to and bind to the surface of the substrate thus providing a permanent record of the separated bands of conjugates on the surface of the membrane.

The electro-blotting procedures which can be used in connection with the present invention are procedures which are generally known to those skilled in the art. In general, a gel having the separated conjugates thereon is placed in contact with a membrane surface. The membrane surface which is preferably a charged nylon surface is preferably first wetted with a buffer in which the electro-blotting procedure will be carried out. What is arbitrarily chosen as the cathode side of the gel (i.e., ultimately towards the negative electrode when positioned in the electro-blotting tank) is placed in contact with the surface of the nylon substrate after the substrate has been moistened with the electro-blotting buffer. Any air bubbles between the gel and the nylon membrane should be removed by gently pushing the nylon substrate against the gel using powder-free gloved fingers. A piece of nitrocellulose can be placed on the opposite side of the gel and all of the air bubbles should be removed between the gel and the nitrocellulose. Such a construct is then placed in the electro-blotting tank which contains a buffer solution and has an anode and a cathode therein. The power supply is then turned on and the power supply will draw the electrically charged saccharide/ANSA conjugates out of the gel and onto the charged surface of the nylon substrate.

The transfer time is dependent somewhat on the thickness of the gel and the size of the conjugates being transferred to the nylon substrate. The transfer can be monitored by viewing the transfer under U.V. light to insure complete transfer of all of the materials to the nylon substrate surface. Overnight transfer is reliable and convenient.

One of the surprising discoveries of the present invention is that the specific bands of conjugates in the gel are even more clearly resolved and distinguishable from each other when the transfer is made to the nylon substrate surface. While not wishing to be bound to any particularly theory, it is believed that greater resolution is obtained on the nylon surface because of the diffusion of light in the gel when the conjugates are exposed to U.V. light. Regardless of the reason, it has been found that distinct, separate bands of conjugates are formed on the nylon substrate surface.

After the conjugates have been secured to the membrane surface, the membrane is exposed to light of a sufficient frequency and for a sufficient time in order to activate the light-sensitive azido-groups attached to the ANSA molecules. Once the azido-groups attach to the ANSA molecules they are activated they provide an active group which tightly binds the conjugate to the nylon substrate surface. This binding is particularly important when the conjugates do not have a particularly large charge. For example, when the saccharide compounds being separated are substantially neutral with respect to charge, they will not bind very tightly to the nylon substrate surface. Accordingly, the light-activated azido-group provides for a secure binding of the conjugates to the nylon substrate surface so that the conjugates are not washed away during any subsequent washing steps.

It is important that the saccharide/ANSA conjugates are securely bound to the nylon substrate surface in that these conjugates are to be used as receptors for labeled probes such as labeled proteins. When the labeled proteins are contacted to the substrate surface, they are allowed to stay in place for a sufficient time to allow for binding to occur between the probe and the saccharide/ANSA conjugate. However, in order to make the assay meaningful, the nylon substrate surface must be thoroughly washed in order to remove any probes which have not securely bound to the saccharides. During this washing procedure, the saccharide/ANSA conjugates would themselves be washed away if they were not securely bound to the nylon substrate surface. If such conjugates were washed away, the sensitivity and accuracy of the assay would, of course, be substantially decreased.

Based on the above, it can be understood that the attachment of the light-sensitive azido-group is a particularly important aspect of the present invention. The azido-group can be attached to any position on the rings of the ANSA which is not occupied. The attachment can be carried out by utilizing reaction schemes and reagents readily known to those skilled in the art. It is possible to attach the azido-group directly to the ring structure or attach the azido-group via a linking group. Procedures for carrying out such attachments are described within the literature.

After the conjugates on the membrane surface have been secured to the surface, the specific saccharides within each of the visually detectable groups can then be tested for their affinity to other molecules. This testing is generally done by first forming conjugates of molecules to be tested by binding such molecules to a label. For example, protein molecules are bound to a radiolabel. The conjugates of radiolabeled proteins are then brought into contact with the saccharide/ANSA conjugates on the surface of the membrane. If the proteins have an affinity to the saccharides on the membrane, they will bind to the saccharides, thus forming double conjugates, i.e., the saccharide/ANSA conjugates bind to the protein/label conjugates.

After the protein/label conjugates have been allowed to remain in contact with the membrane surface for a sufficient period of time to allow for complete binding, the membranes are washed thoroughly in order to remove any unbound protein. After the unbound proteins are removed, the bound proteins, if any, are detected by utilizing the label attached to the proteins by procedures such as radiography.

The separation methodology of the present invention can be utilized in order to test a variety of different types of compounds for their affinity to the saccharides on the nylon substrate. For example, the invention can be utilized in order to test the affinity of certain lectins for their affinity to the saccharides. Particular types of antireceptor proteins known to be positioned on viruses and to be attachable to certain saccharides on cell surfaces can be tested. Further, the affinity of certain growth factor proteins can be tested. It is believed that the attachment of certain saccharides to growth factor proteins can effect the activity of the growth factor protein in vivo.

The molecules to be tested, such as the protein molecules to be tested for their affinity to saccharides, must, of course, be bound to a label which is later detectable. A variety of different types of labels known to those skilled in the art can, of course, be used. For example, it is possible to utilize radiolabels which are later detected by the use of autoradiography. It is also possible to attach the protein molecules to an antibody which itself is bound to an enzyme such as horseradish peroxidase which can be detected by the addition of reagents which cause a color change. Procedures for attaching the labels to the proteins or other molecules to be assayed are well known to those skilled in the art.

The following examples are provided to as to give those of ordinary skill in the art a complete disclosure and description of how to carry out the separation and assaying steps of the invention and are not intended to limit the scope of what the inventors regard as their invention. Efforts have been made to insure accuracy with respect to numbers used (e.g., amounts, temperature), but some experimental errors and deviations should be accounted for. Unless indicated otherwise, parts or parts by weight, temperature is in degrees centigrade and pressure is at or near atmospheric.

EXAMPLE 1

A modified form of 1-amino-4-naphthalene sulfonic acid (ANSA) is formed by the addition of an azido-group. An appropriate azido-group is chosen and added to the ANSA at the 5, 6, 7 or 8 position of the naphthalene ring system. The azido-group is light-sensitive and therefore, should be kept out of contact with light of a frequency capable of activating the group. After the modified ANSA is formed, the modified ANSA has the ability to react with a reducing sugar via the primary amine of the ANSA at the 4 position of the ANSA and the negative charge is present at the 1 position of the ANSA thus providing for the charge necessary in electrophoretic separation techniques. Charged oligosaccharides are formed by reacting a mixture of oligosaccharides with the modified ANSA. The reaction is carried out in 10 to 100 mM sodium acetate buffer (pH 5.0). The oligosaccharides are present in an amount of 0.01–1 umol/ml and are reacted with the modified ANSA and sodium cyanoborohydride in a ten fold molar excess with respect to the reducing end sugar of the oligosaccharide. The derivatized oligosaccharides are then subjected to electrophoretic resolution in 40% acrylamide/5% bis gels, with a Tris/glycine buffer system (25 mM Tris, 195 mM glycine, pH 8.3). The electrophoretic gel is to be run at 300 volts for approximately 90 minutes. The gels are to be immediately electro-blotted using a Biorad apparatus onto a Zetaprobe membrane (of the type commercially sold by Biorad). The electro-blotting is carried out utilizing standard techniques and 100 volts for one hour with the same Tris/glycine buffer system. After completing the electroblotting, the Zetaprobe membranes are removed and air dried. The membranes are then exposed to light which activates the azido-groups thus providing for an active group which tightly binds to the membrane surface. Accordingly, the dried membranes have the highly resolved bands of saccharide/modified ANSA conjugates bound tightly thereon.

For purposes of a comparison, it is preferable to cut the Zetaprobe membranes into a plurality of lanes. This cutting provides multiple copies of the highly resolved saccharide/ANSA conjugate groups. These highly resolved groups are clearly visible under ultraviolet light due to the presence of the shared double bonds within the ring structures of the ANSA.

After the azido-groups are activated and the conjugates are bound by the light activation procedure, they may be probed with proteins (radioiodinated bFGF) overnight at 4° C., in PBS plus 2% PVP40. After allowing any binding to take place, the membrane are washed with the same buffer three times, and then dried. Bound protein can be detected by autoradiography. The ANSA fluorescent label on the oligosaccharide will allow for the direct visualization of the blot and comparison of it with the autorad, i.e., the membrane having the radiolabeled proteins bound thereto.

The above procedure is particularly useful with respect to the resolution of different saccharides which are relatively small in size, e.g., mono-, di- and trisaccharides. This is particularly true when the saccharides in the mixture of saccharides being tested are relatively neutral in charge. The procedure allows for the assaying of large numbers of saccharides by a relatively simple and inexpensive procedure. Further, once large numbers of saccharides are resolved via the present procedure, it is possible to readily test the affinity of these saccharides to large numbers of proteins. Accordingly, the present invention provides not only a means for separating and resolving large numbers of saccharides of different types from one another, but provides a further means for assaying for the affinity of specific resolved saccharides to specific proteins and/or other compounds which may have an affinity to such saccharides.

The instant invention is shown and described herein in what is considered to be the most practical, and preferred embodiments. It is recognized, however, that departures may be made therefrom which are in the scope of the invention and that obvious modifications will occur to one skilled in the art upon reading this disclosure.

We claim:

1. A method of separating a mixture of saccharides into distinct detectable groups, comprising the steps of:
   reacting the mixture of saccharides with a modified form of 1-amino-4-naphthalene sulfonic acid to form conjugates, the 1-amino-4-naphthalene sulfonic acid being modified by the addition of a light-sensitive azido-group;
   subjecting the conjugates to gel electrophoresis in an electrophoresis gel for a sufficient period of time to form separate groups of conjugates in the electrophoresis gel;
   electro-blotting the separate groups of conjugates from the electrophoresis gel onto the surface of a membrane; and
   subjecting the conjugates on the membrane to light for a sufficient time and of a light frequency which activates the light-sensitive azido-group.

2. The method as claimed in claim 1, further comprising:
   contacting the separate groups of conjugates on the membrane with labeled probes to determine the affinity of the probes to bind to a group of conjugates.

3. The method as claimed in claim 2, further comprising:
   washing away any labeled probes not bound to a group of conjugates and detecting bound probes by their label.

4. The method as claimed in claim 2, wherein the labeled probe is a labeled protein probe.

5. The method as claimed in claim 4, wherein the label is a radiolabel.

6. The method as claimed in claim 4, wherein the labeled protein probe is a labeled antireceptor protein of a virus.

7. The method as claimed in claim 4, wherein the electrophoresis gel is comprised of about 40% acrylamide, about 5% bis gels, in a Tris-glycine buffer system.

8. The method as claimed in claim 7, wherein the Tris-glycine buffer system includes approximately 25 mM Tris, approximately 195 mM glycine and has a pH of about 8.3.

9. The method as claimed in claim 1, wherein the azido-group is bound to the naphthalene ring system of the ANSA at the 5, 6, 7 or 8 position.

10. A method as claimed in claim 9, wherein the azido-group is connected directly to the naphthalene ring system.

11. A method as claimed in claim 9, wherein the azido-group is connected to the naphthalene ring system via a linking group.

12. The method as claimed in claim 1, wherein the saccharide mixture includes saccharides selected from the group consisting of mono-saccharides, di-saccharides and trisaccharides.

13. The method as claimed in claim 12, wherein the saccharide is a monosaccharide.

14. The method as claimed in claim 12, wherein the saccharide is an disaccharide.

15. The method as claimed in claim 12, wherein the saccharide is a trisaccharide.

16. A method of resolving a mixture of saccharides into distinct groups of closely related or identical saccharides, comprising the steps of:

reacting the mixture with a modified form of 1-amino-4-naphthalene sulfonic acid to form modified conjugates, the 1-amino-4-naphthalene sulfonic acid being modified by the addition of a light-sensitive azido-group at the 5, 6, 7 or 8 position of the naphthalene ring system of the 1-amino-4-naphthalene sulfonic acid;

subjecting the conjugates to gel electrophoresis in an electrophoresis gel for a sufficient period of time to form separate groups of conjugates in the electrophoresis gel;

electro-blotting the separate groups of conjugates in the electrophoresis gel to a membrane surface; and subjecting the conjugates on the membrane surface to light for a sufficient time and of a light frequency which activates the light-sensitive azido-group and creates a binding between the azido-group and the surface.

17. The method as claimed in claim 16, wherein the membrane is a charged nylon membrane.

18. The method as claimed in claim 17, wherein the saccharide mixture comprises saccharides selected from the group consisting of monosaccharides, disaccharides and trisaccharides.

19. The method as claimed in claim 18, further comprising:
contacting the separate groups of conjugates on the nylon membrane with labeled probes to determine the affinity of the probes to bind to the saccharides in the separate groups.

20. The method as claimed in claim 19, further comprising:
washing away any labeled probes not bound to a saccharide and detecting bound probes by their label.

21. A method for assaying for the affinity of a protein for a saccharide in a mixture of saccharides, comprising the steps of:
reacting the mixture of saccharides with a modified form of 1-amino-4-naphthalene sulfonic acid to form conjugates, the 1-amino-4-naphthalene sulfonic acid being modified by the addition of a light-sensitive azido-group;

subjecting the conjugates to gel electrophoresis in an electrophoresis gel for a sufficient period of time to form separate groups of conjugates in the electrophoresis gel;

electro-blotting the separate groups of conjugates from the gel onto the surface of a membrane;

subjecting the conjugates on the membrane to light for a sufficient time and of a light frequency which activates the light-sensitive azido-group which binds to the surface of the membrane; and contacting the membrane having the conjugates thereon with labeled proteins to determine the affinity of the proteins to bind to saccharides on the membrane.

22. The method as claimed in claim 21, further comprising:
washing away any labeled proteins not bound to saccharides on the membrane surface and detecting bound proteins.

* * * * *